United States Patent [19]

Koyama et al.

[11] Patent Number: 5,120,658
[45] Date of Patent: Jun. 9, 1992

[54] THERMOSTABLE TRYPTOPHAN SYNTHETASE GENE AND EXTREMELY THERMOPHILIC PLASMID VECTOR INCORPORATING SAID GENE

[75] Inventors: Yoshinori Koyama; Kensuke Furukawa, both of Tsukuba; Noboru Tomizuka, Okayama, all of Japan

[73] Assignees: Agency of Industrial Science & Technology; Ministry of International Trade & Industry, both of Tokyo, Japan

[21] Appl. No.: 329,765

[22] Filed: Mar. 28, 1989

[30] Foreign Application Priority Data

Jun. 30, 1988 [JP] Japan .................. 63-163779

[51] Int. Cl.⁵ .................. C12N 15/70; C12N 15/52
[52] U.S. Cl. .................. 435/320.1; 435/69.1;
435/71.2; 435/91; 435/108; 435/172.1;
435/172.3; 435/183; 435/252.3; 536/27; 935/6;
935/9; 935/22; 935/29; 935/59; 935/60;
935/61; 935/66; 935/72
[58] Field of Search ............ 536/27; 435/108, 91,
435/71.2, 183, 69.1, 172.1, 172.3, 252.3, 320.1;
935/6, 9, 22, 29, 59, 60, 61, 66, 72

[56] References Cited

U.S. PATENT DOCUMENTS 4,885,245 12/1989 Ishida et al. .................. 435/108

OTHER PUBLICATIONS

*Biological Abstracts*, 1986, vol. 81(1), Abstract No. 101530, Shen et al., 1986, Genetics, vol. 112(3):441-458.
Koyama et al., 1986, *J. Bacteriol*, vol. 166(1):338-340.
*Biological Abstracts*, vol. 70(10), Abstr. No. 64271, Nagahari et al., 1980, Gene, 10(2):137-146.
Bard et al., 1983, *Gene*, 26:313-315.
Yanisch-Perron et al, *Gene*, vol. 33, pp. 103-119 (1985).
Stark, *Gene*, vol. 51, pp. 255-267 (1987).
Smith et al., "Enzymes Involved in the Biosynthesis of Tryptophan" in *Methods of Enzymology*, vol. 5, pp. 794-806 (1962).
Koyama et al, *J. of Bacteriology*, vol. 172, pp. 3490-3495 (1990).
Koyama et al, *FEMS Microbiology Letters*, vol. 72, pp. 97-102 (1990).
Birge, *Bacterial and Bacteriophage Genetics*, 2nd Ed., Springer-Verlag, N.Y., pp. 34 and 302-307 (1988).
Stryer, *Biochemistry*, 3rd Ed., W. H. Freeman, N.Y., p. 586 (1988).

Primary Examiner—Richard C. Peet
Attorney, Agent, or Firm—Oblon, Spivak, McClelland, Maier & Neustadt

[57] ABSTRACT

A DNA segment, specifically a thermostable tryptophan synthetase gene originating in the strain of extremely thermophilic Thermus aquaticus T2, characterized by the restriction enzyme map of FIG. 1, and not cleaved by specific restriction enzymes.

An extremely thermophilic plasmid vector pYK 105, having the DNA segment and an *Escherichia coli* plasmid vector pUC 13 incorporated in a cryptic plasmid pTT8.

2 Claims, 4 Drawing Sheets

THERMOSTABLE TRYPTOPHAN SYNTHETASE GENE AND EXTREMELY THERMOPHILIC PLASMID VECTOR INCORPORATING SAID GENE

BACKGROUND OF THE INVENTION

1. Field of the Invention

This invention relates to a thermostable tryptophan synthetase gene originating in extremely thermophilic microorganism and an extremely thermophilic microorganism plasmid vector incorporating the gene as a marker therein.

The tryptophan synthetase is an enzyme which synthesizes tryptophan, an essential amino acid, from indole and serine. The gene of this enzyme can be used for inexpensive production of tryptophan. The plasmid vector can be used for breeding an extremely thermophilic microorganism by genetic manipulation.

2. Prior Art Statement

Extremely thermophilic microorganisms capable of growing at high temperatures over 75° C. produce biopolymers which are stable against of heat and exhibit high tolerance to chemical reagents and organic solvents. Therefore, studies have been made on use of the microorganisms in fermentative production at elevated temperatures and on bioreactors by immobilizing the microorganisms or their enzymes. Efficient breeding of such extremely thermophilic microorganisms is an essential requirement for such purposes. While recombinant DNA technique is the most promising means of breeding at present, this method cannot be used with extremely thermophilic microorganisms because they have no antibiotic-resistant plasmid, e.g., they have no plasmid vector.

The inventors have already developed a method for transformation, i.e. a technique for the introduction of a gene DNA, with respect to *Thermus thermophilus* HB 27, a typical species of gram-negative extremely thermophilic microorganisms [Japanese Patent Public Disclosure SHO 60(1985)-188076]. They have also succeeded in separating the 3.1 Kb DNA segment including a tryptophan synthetase gene [Japanese Patent Application SHO 62(1987)-297129]and have studied the feasibility of coupling the DNA segment mentioned above with the cryptic plasmid of a microorganism of genus Thermus and utilizing the product of the coupling as a selective marker gene. They have failed to produce a vector plasmid, however, because the DNA segment in the strain of *Thermus thermophilus* HB 27 as the host frequently undergoes recombination with the chromosome DNA and eventual incorporation in the chromosome DNA and cannot be used as a selective marker.

OBJECT AND SUMMARY OF THE INVENTION

As a result of studying various microorganisms of genus Thermus, the inventors have succeeded for the first time in the art in extracting from the strain of *Thermus aquaticus* T2 (ATCC 27737) a DNA segment which induces hardly any recombination with the chromosome DNA in the strain of *Thermus thermophilus* HB 27 and which contains a thermostable tryptophan synthetase gene.

They have further succeeded in creating a plasmid vector possessing a selective marker in the microorganisms of genus Thermus by coupling the DNA segment and an *Escherichia coli* plasmid vector pUC 13 with the cryptic plasmid pTT8 (originating in the strain of *Thermus thermophilus* HB 8) having no selective marker.

To be specific, this invention is directed to a DNA segment of the length of 3.1 Kb possessing the genetic information of the thermostable tryptophan synthetase of the strain of extremely thermophilic microorganism *Thermus aquaticus* T2 and characterized by such a restriction enzyme cleavage map as illustrated in FIG. 1 and a novel plasmid vector pYK 105 of a microorganism of genus Thermus produced by coupling the DNA segment with the cryptic plasmid pTT8.

The above and other objects and features of the invention will become more apparent from the following detailed description with reference to the accompanying drawings.

DETAILED DESCRIPTION OF THE PREFERRED EMBODIMENTS

The present invention will now be described in detail.

A thermostable tryptophan synthetase gene which only sparingly undergoes recombination with the chromosomal DNA of the strain of *Thermus thermophilus* HB 27 can be separated from a microorganism of genus Thermus which has low affinity for the microorganism mentioned above.

It has been known that the strain of *Thermus aquaticus* T2 (ATCC 27737) taxonomically has remote affinity for the strain of *Thermus thermophilus* HB 27. In fact, when the tryptophan synthetase gene mutant of the strain HB 27 is transformed by the use of the chromosome DNA of the strain T2, the efficiency of transformation to Trp+ is lower than 1/5,000 of the efficiency obtained with the wild chromosome DNA of HB 27. This fact implies that the DNA sequence of the strain T2 in the neiborhood of the tryptophan synthetase gene and the DNA sequence of the strain HB 27 do not easily undergo recombination because they have low homology.

The tryptophan synthetase gene of the strain of T2 is separated by colony hybridization using as a probe therefor the already separated equivalent gene of the strain of *Thermus thermophilus* HB 27. Clones of even low homology can be separated by performing the hybridization under mitigated conditions.

Figure 2:
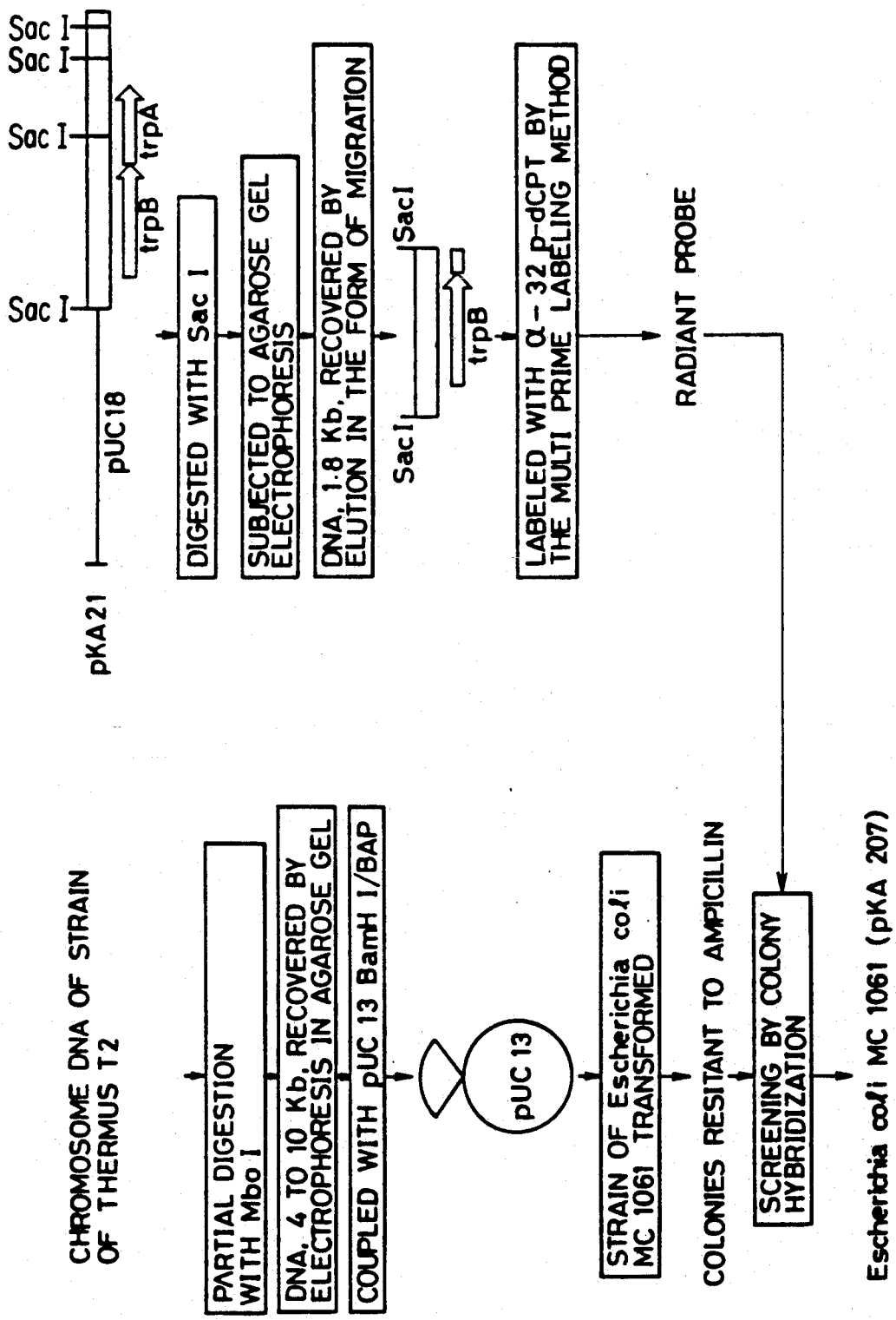
FIG. 2 is a process diagram illustrating the separation of the pKA 270 plasmid cloned by the tryptophan synthetase gene of the strain of *Thermus aquaticus* T2.

The cloning is carried out by a procedure illustrated schematically in FIG. 2.

First, the preparation of the probe DNA will be described below. The tryptophan synthetase gene of the strain of *Thermus thermophilus* HB 27 is cloned on the pKA 21 plasmid retained by the strain of *Escherichia coli* JM 83 (pKA 21) (FERM P-9685). This gene is present at the position illustrated on the restriction enzyme map shown in the right upper part of FIG. 2. The DNA segment containing a trpB gene is separated by digesting the plasmid with a restriction enzyme, Sac I, subjecting the product of digestion to electrophoresis in agarose gel, excising the 1.8 Kb portion of the DNA segment from the product of electrophoresis, and eluting it by migration. This DNA segment is labeled with an $\alpha$-$^{32}$P-dCTP by the multi-prime labeling method and used as the probe for the colony hybridization to be described below.

Now, the preparation of the chromosome DNA library of the strain of Thermus aquaticus T2 for colony hybridization will be described.

The chromosome DNA of the strain of Thermus aquaticus T2 is separated by a conventional method such as the phenol method and then refined. To be more specific, the strain of T2 is cultured, collected from the culture medium, and left standing in a lysozyme solution at a stated temperature for a prescribed period. The cells thus obtained are lysed with an SDS solution and then treated with phenol to extract the DNA. The DNA is recovered by precipitation with ethanol and then treated with a R Nase for isolation of the chromosome DNA.

The chromosome DNA is partially digested with a restriction enzyme, Mbo I, and the 4 to 10 Kb DNA segment is separated by elution in the form of migration. This DNA segment and the pUC 13 plasmid DNA digested with a restriction enzyme, BamH I, and then treated with phosphatase are coupled by virtue of a T4 DNA ligase.

The strain of Escherichia coli MC 1061 is transformed by a treatment with calcium chloride in the presence of the recombined DNA (Escherichia coli plasmid vector) obtained by the procedure described above. Colonies of the transformed strain are obtained by the culture of the strain in an agar medium containing Ampicillin.

From these colonies, a positive clone is selected by screening the colonies in accordance with the colony hybridization using the aforementioned labeled probe.

The transformed strain of Escherichia coli MC 1061 (pKA 207) obtained as described above has been deposited at Fermentation Research Institute, Agency of Industrial Science and Technology (under FERM BP-1924). A plasmid DNA has been prepared from this strain and a simple restriction enzyme map produced (shown at the top of FIG. 3). The pKA 207 is possessed of an insert DNA of 6.8 Kb.

Since the coding frame of the tryptophan synthetase gene has a size of about 2 Kb, it is sub-cloned to the well-known plasmid pTTQ18 possessed of a tac promoter to estimate the position of the tryptophan synthetase gene on the pKA 207 plasmid.

Figure 3:
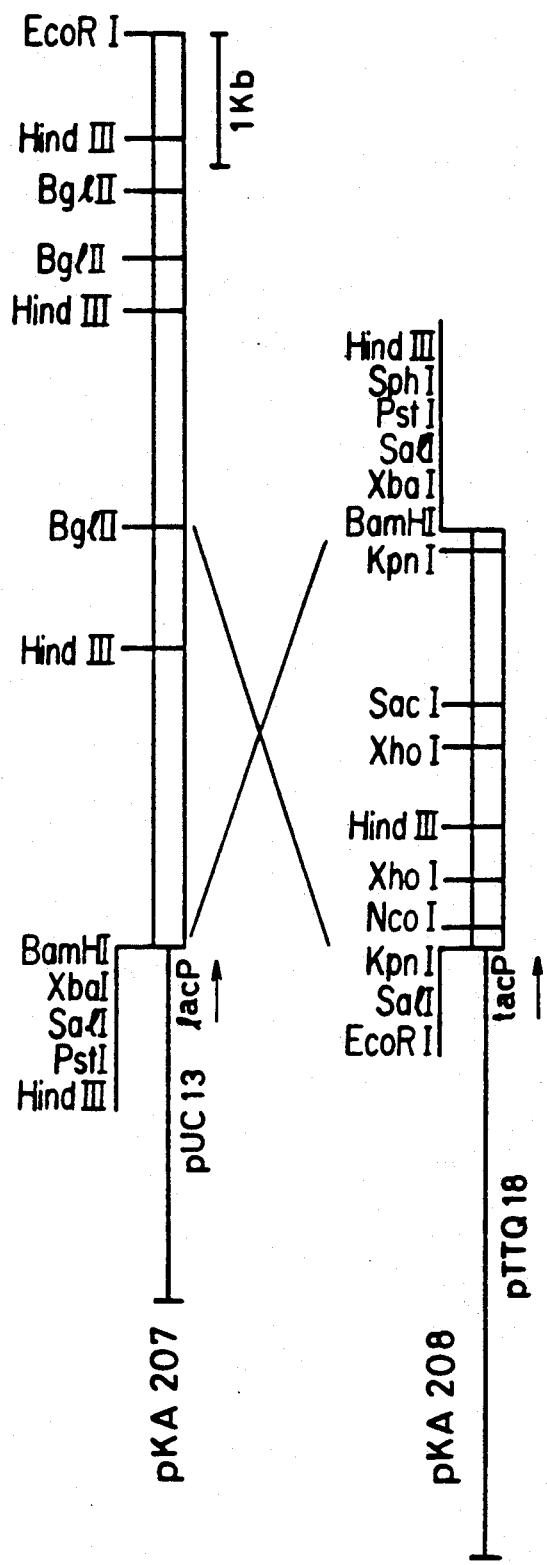
FIG. 3 is a diagram showing the relation between the restriction enzyme map of the pKA 207, pKA 208 plasmid and the inserted DNA.

In the insert DNA of pKA 207, the DNA segment of a length of 3.1 Kb to the left of the Bgl II site at the leftmost part of the restriction enzyme map shown in the upper side in FIG. 3 is sub-cloned. For the purpose of this sub-cloning, the DNA is recovered by digesting the pKA 207 DNA with Bgl II, Pst I, subjecting the product of digestion to electrophoresis in an agarose gel, excising the DNA segment of 3.1 Kb from the product of electrophoresis, and eluting it by migration. The pTTQ18 DNA digested with BamH I and Pst I and the recovered DNA are coupled by virtue of the T4 DNA ligase and then the strain of Escherichia coli MV 1184 is transformed. As a result, the strain of Escherichia coli MV 1184 (pKA 208) is separated and the pKA 208 plasmid DNA is prepared from this strain.

The direction of the insert DNA to the promotor of the plasmid vector is reverse from that of the pKA 208 plasmid and in the pKA 207 (shown at the bottom of FIG. 3).

Figure 1:
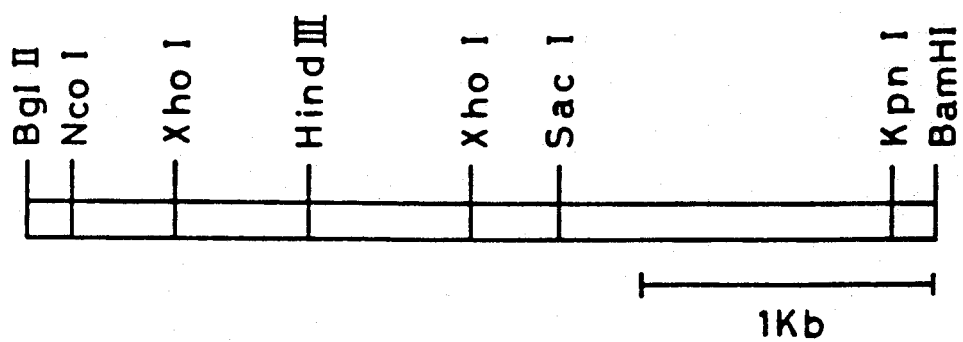
FIG. 1 is a restriction enzyme map of the DNA segment which is a thermostable tryptophan synthetase gene of the present invention.

By an elaborate restriction enzyme analysis, the insert DNA of the pKA 208 has been demonstrated to be a DNA segment of a length of 3.1 Kb not cleaved by the restriction enzymes of Cla I, EcoR I, EcoR V, Hpa I, Mlu I, Pst I, Pvu II, Sal I, Sph I, and Xba I, shown in the restriction enzyme map of FIG. 1.

This DNA segment has been separated from the strain of Thermus aquaticus T2 for the first time by the inventors. It is clearly different in the manner of cleavage with such restriction enzymes as BamH I, Hind III, Nco I, and Pvu II from the formerly separated DNA segment originating in the strain of Thermus thermophilus HB 27 and containing a tryptophan synthetase gene.

The presence of a tryptophan synthetase gene on the insert DNA of the pKA 208 plasmid has been ascertained to the inventors by their observation of an enzyme activity manifested in Escherichia coli.

The strain of Escherichia coli MV 1184 (pKA 208) retaining the pKA 208 plasmid is cultured in a nutrient culture medium containing isopropyl-$\beta$-D-thiogalactoside (IPTG). The cells are collected from the culture broth, suspended in a buffer, and disintegrated by ultrasonic treatment. The suspension is centrifuged. The resultant supernatant is further treated at 80° C. to inactivate the enzyme originating in the Escherichia coli. The supernatant resulting from the centrifugal separation is collected. By the test for tryptophan synthetase activity at the high temperature of 70° C. in accordance with the method proposed by Yanofsky et al. [Methods in Enzymology, Vol. 5, p. 794 (1962)], the supernatant as a crude enzyme solution is found to possess activity at the high temperature and confirmed to comprise a tryptophan synthetase gene deposited on the insert DNA of the pKA 208 plasmid and possess an ability to produce in Escherichia coli a thermostable tryptophan synthetase of a Thermus microorganism.

Once there has been cloned the DNA segment of the tryptophan synthetase gene of the strain of Thermus aquaticus T2 which induces substantially no recombination with the chromosome DNA of the strain of Thermus thermophilus HB 27 as described above, a plasmid vector which is selectable when the tryptophan synthetase gene mutant of the strain of Thermus thermophilus HB 27 is a host, is prepared.

Figure 4:
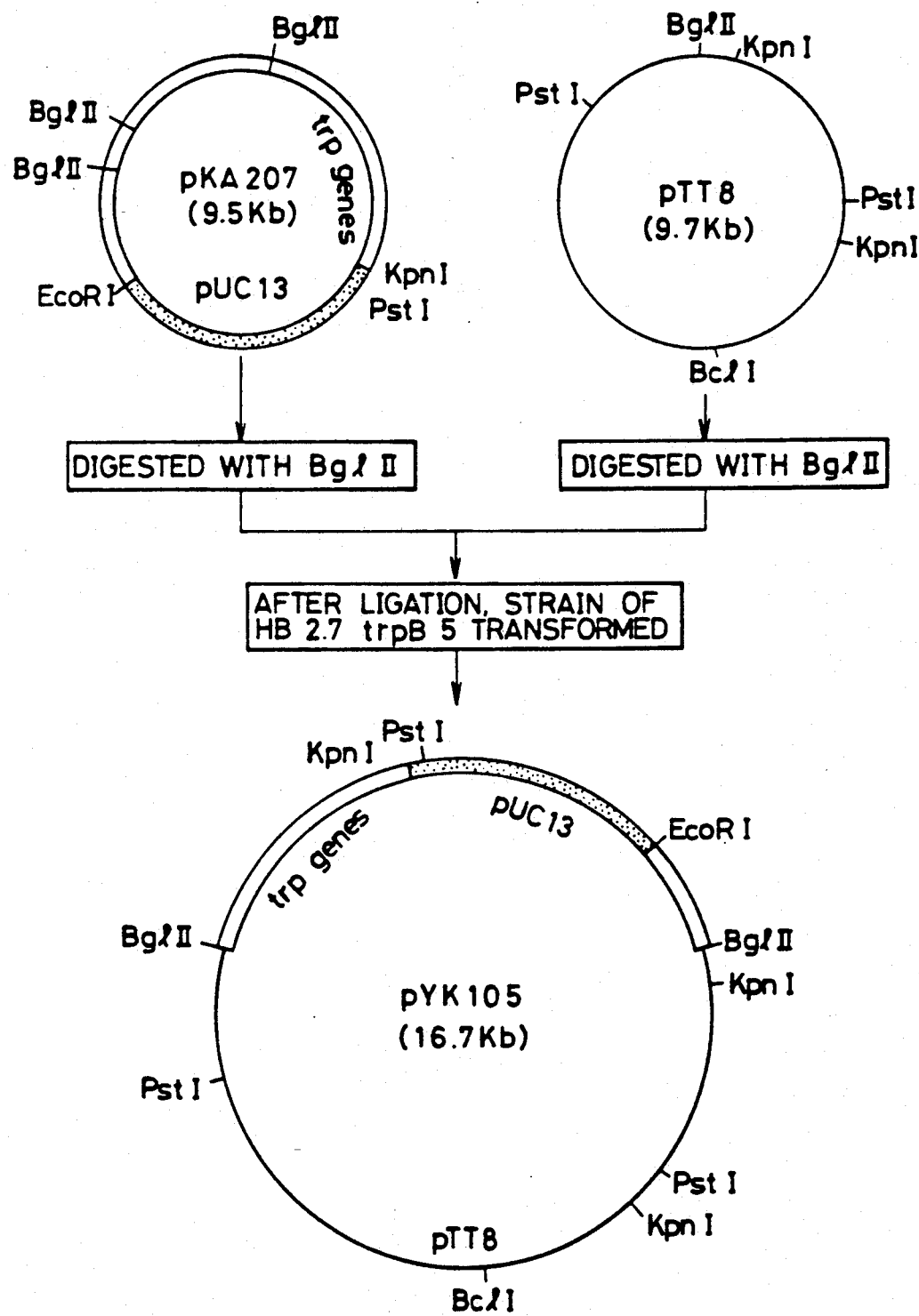
FIG. 4 is a process diagram illustrating the formation of the plasmid vector pYK 105 of the extremely thermophilic microorganism.

The procedure for this preparation is illustrated schematically in FIG. 4. What is obtained by digesting the pKA 207 with the restriction enzyme Bgl II and what is obtained by digesting the cryptic plasmid pTT8 originating in the strain of Thermus thermophilus HB 8 (ATCC 27634) and possessing no selective marker with Bgl II are mixed and coupled by the use of a T4 DNA ligase. With this DNA, the tryptophan synthetase mutant (tryptophan-demanding strain) is transformed. This transformation is carried out by placing the DNA in a culture broth and culturing it therein for one hour by utilizing the fact that a microorganism of genus Thermus naturally possesses an ability for transformation. When the microorganism of genus Thermus containing no tryptophan is applied to the minimum culture medium and cultured thereon at 70° C. for two days, there is obtained a transformed strain of Thermus thermophilus HB 27 trp$^-$ (pYK 105) which no longer requires tryptophan.

The plasmid pYK 105 separated from the transformed possesses the structure illustrated at the bottom of FIG. 4.

The plasmid pYK 105 separated from the transformed strain possesses the structure illustrated at the bottom of FIG. 4. Since it possesses the pUC 13 plasmid, it constitutes a shuttle vector which can replicate not only in the microorganism of genus Thermus but also in the *Escherichia coli*. The selection of the transformed strain is attained by virtue of the tolerance to Ampicillin in the case of the *Escherichia coli* and the complementation of the tryptophan-demanding property in the case of the thermophilus strain of *Thermus thermophilus* HB 27 trp⁻. The pYK 105 is the first selectable plasmid vector produced with a microorganism of genus Thermus.

Now, the present invention will be described more specifically below with reference to a working example.

EXAMPLE

(1) Preparation of pKA 21 Plasmid

The strain of *Escherichia coli* JM 83 (pKA 21) [deposited at Fermentation Research Institute, Agency of Industrial Science and Technology under FERM P-9685] having the tryptophan synthetase gene of the strain of *Thermus thermophilus* HB 27 (FERM P-7502) on the plasmid pKA 21 was cultured at 37° C. in 200 ml of a 2 TY culture medium (containing 16 g of Difco trypton, 10 g of yeast extract, and 5 g of NaCl in 1 liter of purified water). The cultured cells were collected, suspended in 4 ml of a solution of 25 mM Tris-Cl (pH 8)−10 mM EDTA−50 mM glucose−0.5% lysozyme, and left standing therein at 37° C. for five minutes. The resultant suspension and 10 ml of a solution of 0.2N NaOH−1% SDS (sodium dodecyl sulfate) added thereto were left standing at 0° C. for 10 minutes. The mixture thus obtained and 7.5 ml of a solution of 5M potassium acetate (pH 4.8) added thereto were left standing at 0° C. for 10 minutes and then centrifuged to produce a supernatant. The supernatant and PEG 6000 added thereto in a final concentration of 10% were left standing at 0° C. for two hours and then centrifuged to induce precipitation of DNA. The precipitated DNA was dissolved in 5 ml of a TE buffer (10 mM Tris-Cl, 1 mM EDTA, pH 7.5) and then subjected to ethidium bromide-cesium chloride equilibrium density gradient centrifugation, to obtain a plasmid DNA. In all the processes described hereinafter, the plasmid was prepared by this procedure.

(2) Preparation of probe DNA from pKA:

For the purpose of excising the trpB part exhibiting high homology among various strains from the pKA 21, 5 μg of the pKA 21 DNA obtained in (1) was digested with 20 units of a restriction enzyme Sac I, the digested product was subjected to electrophoresis in 40 mM Tris−20 mM acetic acid−2 mM EDTA−0.7% agarose, a band of 1.85 Kb DNA was excised from the resultant and the DNA was recovered from the agarose by elution in the form of migration. A radiant DNA probe was prepared by labeling 25 ng of the DNA mentioned above with α-$^{32}$p-dCTP by the use of a random primer DNA labeling kit (produced by Takara Shuzo Co., Ltd.).

(3) Preparation of chromosome DNA of strain *Thermus aquaticus* T2 and digestion thereof with restriction enzyme:

The strain of *Thermus aquaticus* T2 (ATCC 27737) was inoculated to 2 liters of Thermus culture medium (containing 2 g of Difco yeast extract, 4 g of polypepton (Daigo Eiyo), and 1 g of NaCl in 1 liter of purified water and adjusted to pH 7.5). Near the end of the logarithmic growth phase, about 6 g of wet cells were collected from the culture broth. The wet cells were suspended in 6 ml of 0.15M NaCl−0.1 M EDTA (pH 8) having 12 mg of lisozyme dissolved therein, kept heated at 37° C. for 20 minutes, and quickly frozen in a coolant of ethanol dry ice. The cooled suspension and 50 ml of 0.1M tris hydrochloride buffer (pH 9)−1% SDS−0.1M NaCl added thereto were stirred. The stirred mixture and 56 ml of phenol saturated with the aforementioned buffer added thereto were shaken at 4° C. and centrifuged. The supernatant consequently formed was separated. This supernatant was admixed with twice as large a volume of cold ethanol to induce precipitation of threads of nucleic acid fraction. The nucleic acid fraction was dissolved in 20 ml of 0.1×SSC (SSC=0.15M NaCl—0.015M sodium citrate) and then admixed with 2 ml of 10×SSC, to obtain a crude DNA solution. Then, this solution and R Nase A (produced by Sigma Corp) and R Nase T1 (produced by Sigma Corp) added thereto in final concentrations of 50 μg/ml and 30 μg/ml respectively were kept at 37° C. for 30 minutes for decomposition of RNA and the phenol treatment was repeated, to obtain a chromosome DNA solution.

Subsequently, in 0.5 ml of a reaction solution of 10 mM Tris−Cl (pH 7.4)−50 mM NaCl−10 mM MgCl₂, 100 μg of the chromosome DNA and 10 units of Mbo I restriction enzyme added thereto were left reacting at 24° C. for one hour to effect partial digestion and treated with phenol and extracted with ether to effect inactivation of the restriction enzyme. The resultant mixture was subjected to electrophoresis in 0.7% agarose−100 mM Tris−boric acid−2 mM EDTA (pH 8.3). A DNA fraction of a size of about 4 to 10 Kbp was separated by elution in the form of migration, treated with phenol, extracted from chloroform, precipitated with ethanol, and then dissolved in 0.1 ml of TE buffer.

(4) Insertion of chromosome DNA segment in vector DNA:

The vector plasmid pUC 13 of *Escherichia coli* was digested with the restriction enzyme BamH I, mixed with 0.1 μg of a phosphatase-treated DNA [purchased from Pharmacia and reported in "Gene", Vol. 33, p. 103 (1985)] and 1 μg of the chromosome DNA obtained in (3), and caused to react with 1 unit of the T4 DNA ligase at 16° C. for 12 hours in 30 μl of a reaction solution of 50 mM Tris-Cl (pH 7.5)−5 mM MgCl₂−10 mM DTT−0.4 mM ATP, to effect coupling of the vector and the chromosome DNA segment.

(5) Introduction of recombined plasmid into *Escherichia coli* (transformation):

The strain of *Escherichia coli* MC 1061 (Pharmacia Sales Corp) was inoculated to 10 ml of the 2 TY culture medium and cultured therein at 37° C. When the absorbance of the cultured broth at 660 nm reached 0.3, the cells were collected. The cells were suspended in 5 ml of 50 mM CaCl₂, left standing therein at 0° C. for one hour, and centrifuged to collect cells. The cells were suspended again in 1 ml of 50 m M CaCl₂. In 0.2 ml of this suspension, 30 μl of the DNA solution obtained in (4) was left standing at 0° C. for one hour, and cultured in 5 ml of the 2 TY culture medium at 37° C. for one hour. The resultant culture broth was applied to an H agar culture medium (trypton 1%, NaCl 0.8%, pH 7, agar 1.5%) containing Ampicillin (50 μg/ml), and cultured at 37° C. for 15 hours, to obtain ampicillin-resistant *Escherichia coli* transformed colonies.

(6) Selection of recombinant *Escherichia coli* clone containing tryptophan synthetase gene:

The selection of the clone was effected by colony hybridization. The colonies of the transformed strain obtained in (5) were replicated on nitrocellulose filters, then immersed for 10 minutes each sequentially in the four solutions, 0.5M NaOH, 0.5M Tris-Cl (pH 7.5), 1.5M NaCl −0.5M tris-Cl, and 2×SSC, and thereafter heated at 80° C. for three hours.

The filters and 1 ml of a hybridization solution (50% formamide, 4×SSC, 50 mM Tris-Cl, pH 7.5) and the radiant DNA probe obtained in (2) added thereto per filter were left standing at 42° C. for 20 hours.

The filters were washed for 15 minutes each at room temperature once with 4×SSC and twice with 2×SSC, dried in an air stream, and subjected to autoradiography to effect selection of a positive clone.

The recombinant strain obtained as described above was designated as *Escherichia coli* MC 1061 (pKA 207) and deposited at Fermentation Research Institute, Agency of Industrial Science and Technology under FERM BP-1924.

From the recombinant strain, the pKA 207 plasmid DNA was prepared and a simple restriction enzyme map (as shown at the top of FIG. 3) was produced. The insert DNA of the pKA 207 had a length of 6.8 Kb and was not cleaved with EcoR I, Pst I, Sal I, or Xba I.

(7) Construction of sub-clone plasmid pKA 208 from pKA 207:

Since the tryptophan synthetase gene constituted about 2 Kb of the total trpAB, the following sub-cloning was carried out for the purpose of accurate estimation of the position of the gene on the insert DNA of the pKA 207.

The DNA 3.1 Kb in length interposed between the Bgl II site and the Pst I site located on the left most side of the insert DNA of the pKA 207 was subjected to the following sub-cloning.

Five μg of the pKA 207 DNA was digested with 20 units each of Bgl II and Pst I and subjected to electrophoresis in agarose gel. The 3.1 Kb DNA segment of the pKA 207 DNA was excised and the DNA was recovered by elution in the form of migration. The DNA segment mentioned above and 50 ng of the DNA of the tac promotor vector pTTQ18 [produced by Amersham Corp and reported in "Gene", Vol. 51, p. 255 (1987)] digested with the BamH I and Pst I were coupled by virtue of the T4 DNA ligase.

By the use of the resultant coupled DNA, the strain of *Escherichia coli* MV 1184 (purchased from Takara Shuzo Co., Ltd.) was transformed by the same procedure as used in (5).

The recombinant strain obtained as above was designated as *Escherichia coli* MV 1184 (pKA 208). From this strain, the pKA 208 plasmid DNA prepared.

The pKA 208 plasmid (shown at the bottom of FIG. 3) was reverse to the pKA 207 with respect to the direction of the insert DNA relative to the promotor of the plasmid vector.

By more elaborate restriction enzyme analysis, the insert DNA of the pKA 208 was bound to be a DNA segment 3.1 Kb in length shown in the restriction enzyme map of FIG. 1 and not cleaved with the restriction enzymes of Cla I, EcoR I, EcoR V, Hpa I, Mlu I, Pst I, Pvu II, Sal I, Sph I, or Xba I.

This DNA segment has been separated for the first time by the inventors from the strain of *Thermus aquaticus* T2. It is different from the DNA segment originating in the formerly separated the tryptophan synthetase gene of strain of *Thermus thermophilus* HB 27 with respect to the cleavage with such restriction enzymes as BamH I, Hind III, Nco I, and Pvu II. It is obviously a different DNA segment.

(8) Activity of thermostable tryptophan synthetase of *Escherichia coli* retaining pKA 208 plasmid:

The presence of the tryptophan synthetase gene on the insert DNA of the pKA 208 plasmid has been confirmed by the enzymatic activity manifested in *Escherichia coli*.

The strain of *Escherichia coli* MV 1184 (pKA 208) retaining the pKA 208 plasmid was inoculated to the 2 TY culture medium (containing IPTG at a concentration of 120 μg/ml) and cultured therein at 37° C. to the stationary phase. The cells were collected and suspended in a buffer of 100 mM Tris-Cl (pH 7.8) and disintegrated by the ultrasonic treatment. The suspension was centrifugally separated. The supernatant was heat-treated at 80° C. to inactivate the enzyme originating in the *Escherichia coli*. The supernatant resulting from the centrifugal separation was separated and used as an enzyme solution.

Ten μl of the enzyme solution and 1 ml of a reaction solution (100 mM Tris-Cl (pH 7.8)−0.4 mM indole −80 mM DL serin−180 mM NaCl−0.03 mM pyridoxal phosphoric acid) added thereto were left reacting at 70° C. for 20 minutes. The reaction was stopped by addition of 0.1 ml of 0.1N NaOH. The reaction solution was treated with 4 ml of toluene to extract the indole. One ml of the resultant reaction solution, 2 ml of a coloring solution (prepared by dissolving 9 g of p-dimethylbenzaldehyde in 200 ml of ethanol, admixing the resultant solution with 45 ml of concentrated hydrochloric acid, and diluting the resultant mixture with ethanol to a total volume of 250 ml) and 4 ml of 95% ethanol added thereto were left standing for 20 minutes and colorimetrically assayed for absorbance at 540 nm. By this method, the residual amount of the indole was determined and the tryptophan synthetase activity was examined.

In the test, the enzyme solution of *Escherichia coli* retaining the pKA 208 showed a conspicuous thermostable tryptophan synthetase activity as compared with the enzyme solution of *Escherichia coli* retaining only the pTTQ18 vector as a control.

Thus, it was confirmed that the thermostable tryptophan synthetase gene originating in the strain of *Thermus aquaticus* T2 was present on the insert DNA of the pKA 208 plasmid and that the thermostable tryptophan synthetase of the Thermus microorganism was produced in the *Escherichia coli* retaining the pKA 208.

(9) Construction of plasmid vector pYK 105 for Thermus bacteria:

The vector was constructed by the procedure illustrated in the schema in FIG. 4. What was obtained by digesting 1 μg of the pKA 207 DNA with the restriction enzyme Bgl II and what was obtained by digesting 1 μg of the cryptic plasmid pTT8 DNA prepared from the strain of *Thermus thermophilus* HB 8 (ATCC 27634) and having no selective marker were mixed and left reacting at 16° C. for eight hours in the presence of 1 unit of the T4 DNA ligase, to be coupled. By the use of the DNA consequently obtained, the strain of *Thermus thermophilus* HB 27 Trp⁻ (deposited at Fermentation Research Institute, Agency of Industrial Science and Technology under FERM P-7507), i.e. a tryptophan synthetase gene mutant (tryptophan-demanding strain) was transformed. The culture broth obtained by culturing the strain mentioned above overnight was inoculated in 1% to a Thermus culture medium and cultured at 70° C. for two hours.

The resultant culture broth was diluted with physiological saline water (0.9% NaCl) and applied to minimum synthetic agar culture medium for a microorganism of genus Thermus (prepared by adding 5 g of sucrose, 0.5 g of $K_2HPO_4$, 0.25 g of $KH_2PO_4$, 2 g of NaCl, 2.5 of $(NH_4)_2SO_4$, 100 μg of biotin, 1 mg of thiamine hydrochloride, 0.125 of $MgCl.6H_2O$, 25 mg $CaCl_2.2H_2O$, 6 mg of $FeSO_4.7H_2O$, 0.8 mg of $CoCl_2.6H_2O$, 20 μg of $NiCl_2.6H_2O$, 1.2 mg of $NaMoO_2.2H_2O$, 0.1 mg of $VOSO_4.3H_2O$, 0.5 mg of $MnCl_2.4H_2O$, 60 μg of $ZnSO_4.7H_2O$, 15 μg of $CuSO_4.5H_2O$, and 15 g of agar (Nakarai Kagaku) to 1 liter and diluting the resultant mixture to pH 7.2).

When this culture was continued at 70° C. for two days, there was obtained a transformed strain of *Thermus thermophilus* HB 27 trp⁻ (pYK 105) no longer demanding tryptophan. The plasmid pYK 105 separated from the transformed strain possessed the structure illustrated at the bottom of FIG. 4. Since it possessed a pUC 13 plasmid, it constituted a shuttle vector which can replicate not only in the microorganism of genus Thermus but also in the *Escherichia coli*. The selection of the transformed strain could be effected by virtue of the ampicillin resistance in the case of the *Escherichia coli* and by virtue of the complementation of the tryptophan-demanding property in the case of the thermophilic strain of *Thermus thermophilus* HB 27 trp⁻. The pYK 105 is the first selectable plasmid vector constructed for the microorganism of genus Thermus.

The thermostable tryptophan synthetase gene separated by this invention permits the thermostable tryptophan synthetase to be produced abundantly from *Escherichia coli*.

The plasmid vector pYK 105 allows genetic engineering of the strain of *Thermus thermophilus* HB 27.

What is claimed is:

1. An isolated DNA segment comprising a gene encoding tryptophan synthetase isolated from *Thermus aquaticus* T2, characterized by the restriction enzyme map of FIG. 1, whereby the gene is not cleaved by at least by Cla I, EcoR I, EcoR V, Hpa I, Mlu I, Pst I, Pvu II, Sal I, Sph I, and Xba I, whereby said DNA segment comprises a length of 3.1 Kb.

2. A thermophilic plasmid vector pYK105, having an *Escherichia coli* plasmid vector pCU13 in a cryptic plasmid pTT8 in combination with a DNA segment comprising a gene encoding tryptophan synthetase isolated from *Thermus aquaticus* T2, characterized by the restriction enzyme map of FIG. 1, whereby said DNA segment is not cleaved at least by Cla I, EcoR I, EcoR V, Hpa I, Mlu I, Pst I, Pvu II, Sal I, Sph I, and Xba I, whereby said DNA segment comprises a length of 3.1 Kb.

* * * * *

UNITED STATES PATENT AND TRADEMARK OFFICE
CERTIFICATE OF CORRECTION

PATENT NO.   : 5,120,658
DATED        : June 9, 1992
INVENTOR(S)  : Yoshinori Koyama et al.

It is certified that error appears in the above-identified patent and that said Letters Patent is hereby corrected as shown below:

On the title page, Assignee:    Item[73], should be, --Agency of Industrial Science & Technology, Ministry of International Trade & Industry, Tokyo, Japan--.

Signed and Sealed this

Third Day of August, 1993

Attest:

MICHAEL K. KIRK

*Attesting Officer*          Acting Commissioner of Patents and Trademarks